(12) United States Patent
Laurencin et al.

(10) Patent No.: US 8,758,437 B2
(45) Date of Patent: *Jun. 24, 2014

(54) MECHANICALLY COMPETENT SCAFFOLD FOR LIGAMENT AND TENDON REGENERATION

(71) Applicant: Soft Tissue Regeneration, Inc., New Haven, CT (US)

(72) Inventors: Cato T. Laurencin, Avon, CT (US); Mark T. Aronson, Midlothian, VA (US); Lakshmi Sreedharan Nair, Avon, CT (US)

(73) Assignee: Soft Tissue Regeneration, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/693,878

(22) Filed: Dec. 4, 2012

(65) Prior Publication Data
US 2013/0096679 A1 Apr. 18, 2013

Related U.S. Application Data

(63) Continuation of application No. 12/649,913, filed on Dec. 23, 2009, now Pat. No. 8,486,143.

(60) Provisional application No. 61/180,732, filed on May 22, 2009, provisional application No. 61/181,033, filed on May 26, 2009.

(51) Int. Cl.
*A61F 2/08* (2006.01)

(52) U.S. Cl.
USPC ............................................ 623/13.14

(58) Field of Classification Search
CPC ............................................ A61F 2/08
USPC ................................. 623/13.11–13.2
See application file for complete search history.

(56) References Cited

U.S. PATENT DOCUMENTS

| | | | |
|---|---|---|---|
| 3,797,047 | A | 3/1974 | Pillet |
| 4,043,344 | A | 8/1977 | Landi |
| 4,187,558 | A | 2/1980 | Dahlen |

(Continued)

FOREIGN PATENT DOCUMENTS

| | | |
|---|---|---|
| AU | 2001249322 | 10/2001 |
| CA | 2403983 | 10/2001 |

(Continued)

OTHER PUBLICATIONS

Aoki, et al., "Transfer of latissimus dorsi for irreparable rotator-cuff tears.", J. Bone Joint Surg. Br., 78(5):761-766 (1996).

(Continued)

*Primary Examiner* — Suzette J Gherbi
(74) *Attorney, Agent, or Firm* — Pabst Patent Group LLP

(57) ABSTRACT

A multi-region device for repair, regeneration or reconstruction in articular tissue injury such as torn ligaments and tendons is provided. The device comprises at least one degradable material and biocompatible non-degradable polymeric fiber-based material, in a three-dimensional braided scaffold. The two end sections are designed for attachment of the device at the site of implantation and are designed to allow bone cell ingrowth, and one or more middle regions are designed to allow ligament or tendon cell ingrowth.

15 Claims, 2 Drawing Sheets

(56) References Cited

U.S. PATENT DOCUMENTS

| | | | |
|---|---|---|---|
| 4,483,023 A | 11/1984 | Hoffman, Jr. | |
| 4,610,688 A | 9/1986 | Silvestrini | |
| 4,731,084 A | 3/1988 | Dunn | |
| 4,790,850 A | 12/1988 | Dunn | |
| 4,792,336 A | 12/1988 | Hlavacek | |
| 4,834,755 A | 5/1989 | Silvestrini | |
| 4,946,377 A | 8/1990 | Kovach | |
| 4,987,665 A | 1/1991 | Dumican | |
| 5,061,283 A | 10/1991 | Silvestrini | |
| 5,078,744 A | 1/1992 | Chvapil | |
| 5,147,400 A | 9/1992 | Kaplan | |
| 5,151,104 A | 9/1992 | Kenna | |
| 5,263,984 A | 11/1993 | Li | |
| 5,376,118 A * | 12/1994 | Kaplan et al. | 623/23.72 |
| 5,595,621 A | 1/1997 | Light | |
| 5,718,012 A | 2/1998 | Cavallaro | |
| 6,596,296 B1 * | 7/2003 | Nelson et al. | 424/426 |
| 6,773,459 B2 | 8/2004 | Dauner | |
| 7,854,760 B2 | 12/2010 | Molaei | |
| 7,972,354 B2 | 7/2011 | Prestezog | |
| 8,011,370 B2 | 9/2011 | Karabey | |
| 8,052,744 B2 | 11/2011 | Girton | |
| 8,057,876 B2 | 11/2011 | Wang | |
| 8,070,810 B2 | 12/2011 | Tarrant | |
| 8,142,501 B2 * | 3/2012 | Macossay-Torres | 623/13.2 |
| 8,177,839 B2 | 5/2012 | Koob | |
| 2002/0133229 A1 | 9/2002 | Laurencin | |
| 2004/0059416 A1 | 3/2004 | Murray | |
| 2004/0267362 A1 | 12/2004 | Hwang | |
| 2005/0136764 A1 | 6/2005 | Sherman | |
| 2005/0288797 A1 * | 12/2005 | Howland | 623/23.74 |
| 2007/0162121 A1 | 7/2007 | Tarrant | |
| 2007/0233242 A1 | 10/2007 | Laurencin | |
| 2008/0031923 A1 | 2/2008 | Murray | |
| 2008/0051888 A1 | 2/2008 | Ratcliffe | |
| 2008/0300683 A1 | 12/2008 | Altman | |
| 2009/0054982 A1 | 2/2009 | Cimino | |
| 2009/0292359 A1 | 11/2009 | Borden | |
| 2009/0306775 A1 * | 12/2009 | Macossay-Torres | 623/13.2 |
| 2010/0047309 A1 | 2/2010 | Lu | |
| 2010/0256756 A1 | 10/2010 | Altman | |
| 2010/0292791 A1 | 11/2010 | Lu | |
| 2011/0040388 A1 | 2/2011 | Alini | |
| 2011/0066242 A1 | 3/2011 | Lu | |
| 2011/0238178 A1 | 9/2011 | Downes | |
| 2011/0257744 A1 | 10/2011 | Amaya | |
| 2012/0078369 A1 | 3/2012 | Hart | |

FOREIGN PATENT DOCUMENTS

| | | |
|---|---|---|
| EP | 0122744 | 10/1984 |
| EP | 0334045 | 9/1989 |
| EP | 1272127 | 1/2003 |
| EP | 1493404 | 1/2005 |
| JP | H07506995 | 8/1995 |
| JP | H09500209 | 1/1997 |
| JP | 4452426 | 10/2003 |
| WO | 9415550 | 7/1994 |
| WO | 9501810 | 1/1995 |
| WO | 9527449 | 10/1995 |
| WO | 0172241 | 10/2001 |
| WO | 01072241 | 10/2001 |
| WO | 2007087353 | 8/2007 |

OTHER PUBLICATIONS

Bellincampi, et al., "Viability of fibroblast-seeded ligament analogs after autogenous implantation.", J. Orthop. Res., 16:414-420 (1998).

Bungaro, et al., "Comparative and experimental study on different tendinous grasping techniques in rotator cuff repair: a new reinforced stitch.", Chir. Organi. Mov., 90(2):113-119 (2005).

Friedman, et al., "Autogeneic anterior cruciate ligament (ACL) anterior reconstruction of the knee. A review.", Clin. Orthop. Relat. Res., 196:9-14 (1985).

Gazdag, et al., "Alternatives to Autogenous Bone Graft: Efficacy and Indications.", J. Am. Acad. Orthop. Surg., 3(1):1-8 (1995).

Gerber, "Latissimus dorsi transfer for the treatment of irreparable tears of the rotator cuff.", Clin. Orthop. Relat. Res., 275:152-160 (1992).

Goulet, et al., "Tendons and Ligaments," Principles of Tissue Engineering (Lanza, Langer, and Chick, eds.), R. G. Landes Company and Academic Press, Inc., p. 639-645 (1997).

International Patent Application No. PCT/US2001/09079, International Search Report mailed (Aug. 2, 2001).

Jackson, et al., "Intraarticular reaction associated with the use of freeze-dried, ethylene oxide-sterilized bone-patella tendon-bone allografts in the reconstruction of the anterior cruciate ligament", Am. J. Sports Med., 18(1):1-10 (1990).

Kimura, et al, "Reconstruction of a defect of the rotator cuff with polytetrafluoroethylene felt graft. Recovery of tensile strength and histocompatibility in an animal model", J. Bone Joint Surg. Br., 85(2):282-287 (2003).

Koh, et al., "Supplementation of rotator cuff repair with a bioresorbable scaffold", Am J Sports Med., 30(3):410-413 (2002).

Langer and Vacanti, "Tissue engineering", Science, 260(5110):920-926 (1993).

Lin, et al., "Ligament tissue engineering using synthetic biodegradable fiber scaffolds", Tissue Engineering, 5(5):443-52 (1999).

Shino, et al., "Maturation of allograft tendons transplanted into the knee. An arthroscopic and histological study", J. Bone Joint Surg. Br., 70(4):556-560 (1988).

* cited by examiner

MECHANICALLY COMPETENT SCAFFOLD FOR LIGAMENT AND TENDON REGENERATION

CROSS REFERENCE TO RELATED APPLICATIONS

This application is a continuation of U.S. Ser. No. 12/649,913, filed Dec. 30, 2009, entitled "Mechanically Competent Scaffold for Ligament and Tendon Regeneration", by Cato T. Laurencin, Mark T. Aronson and Lakshmi Sreedharan Nari, which claims priority under 35 U.S.C. 119 to U.S. Ser. No. 61/180,732 filed May 22, 2009, and U.S. Ser. No. 61/181,033 filed May 26, 2009, all of which are herein incorporated in their entirety by reference.

FIELD OF THE INVENTION

The present invention is in the field of implantable medical devices and prosthesis, particularly, devices useful as both a structural prosthetic for articular tissue and an in viva scaffold for the regeneration of articular tissue, including ligaments and tendons, and methods of making and using the devices.

BACKGROUND OF THE INVENTION

Reconstructive surgery is based upon the principle of replacing defective tissues with viable, functioning alternatives. In orthopaedic reconstruction, surgeons often replace damaged tissue resulting from trauma, pathological degeneration, or congenital deformity with autogenous grafts. The grafting of bone in skeletal reconstruction has become a common task of the orthopaedic surgeon with over 863,200 grafting procedures performed each year in the U.S. There are over 1,000,000 procedures of various types for cartilage repair performed each year and there are approximately 200,000 to 250,000 procedures for ligament repair performed per year (Langer and Vacanti, Science, 260 (5110):920-6 (1993)). Currently, autografts (tissue taken from the patient) and allografts (tissue taken from a cadaver) are the most common replacement sources for the treatment of musculoskeletal problems (Friedman, et al. Clin. Ortho., 196:9-14 (1985); Jackson, et al. Amer. J. Sports Med., 18 (1):1-10 (1990); Gazdag, et al. J. Amer. Acad Ortho. Surg., 3 (1):1-8 (1995); Shino et, al. J. Bone and Joint Surg., 70 (4)1:556 (1988) and Jackson, et al. Arthroscopy, 10:442-52 (1994)). In repair of ligament injuries, such as injury of the anterior cruciate ligament (ACL), a segment of the patellar tendon is frequently used (Jackson, et al. Amer. J. Sports Med., 18 (1):1-10 (1990)). Transplantation of autogenous grafts has been the current treatment of choice for cartilage and bone repair.

However, there are various problems associated with these treatments. For example, for autogenous tissue, key limitations are donor site morbidity where the remaining tissue at the harvest site is damaged by removal of the graft, and the limited amount of tissue available for harvesting. Allografts are an attempt to alleviate these problems. However, this type of graft is often rejected by the host body due to an immune response to the tissue. Allografts are also capable of transmitting disease. Although a thorough screening process eliminates most of the disease carrying tissue, this method is not 100% effective. Surgeons have looked to synthetic alternatives as a result of the limitations with conventional reconstructive graft materials.

Synthetic ligament grafts or graft supports include carbon fibers, Leeds-Keio® ligament (polyethylene terephthalate), the Gore Tex® prosthesis (polytetrafluoroethylene), the Stryker-Dacron® ligament prosthesis made of Dacron® tapes wrapped in a Dacron® sleeve and the Gore-Tex® ligament augmentation device (LAD) made from polypropylene. These grafts have exhibited good short term results but have encountered clinical difficulties in long term studies. Limitations of these synthetic ligament grafts include stretching of the replacement material, weakened mechanical strength compared to the original structure and fragmentation of the replacement material due to wear.

Natural ligaments are elongated bundles of collagenous soft tissue that serve, among other things, to hold the component bones of joints together. The desired characteristics for a ligament prosthesis include appropriate size and shape, biological compatibility, capability of being readily attached by the surgeon to the body of the patient, high fatigue resistance and mechanical behavior approximating that of the ligamentous tissue sought to be repaired or replaced.

Ligament constructs comprising collagen fibers, biodegradable polymers and composites thereof have been developed. Collagen scaffolds for ACL reconstruction seeded with fibroblasts from ACL and skin are described for example in Bellincampi, et al. J. Orthop. Res. 16:414-420 (1998) and PCT WO 95/2550. A bioengineered ligament model, which includes addition of ACL fibroblasts to the structure, the absence of cross-linking agents and the use of bone plugs to anchor the bioengineered tissue, has also been described (Goulet et al. Tendons and Ligaments. In R. P. Lanza, R. Langer, and W. L. Chick (eds), Principles of Tissue Engineering, pp. 639-645, R. G. Landes Company and Academic Press, Inc. 1997). U.S. Patent Application No. 20020123805 by Murray, et al. describes the use of a three-dimensional (three dimensional) scaffold composition which includes an inductive core made of collagen or other material, for repairing a ruptured anterior cruciate ligament (ACL) and a method for attaching the composition to the ruptured anterior cruciate ligament (See also U.S. Patent Application No. 20040059416). WO 2007/087353 discloses three-dimensional scaffolds for repairing torn or ruptured ligaments. The scaffold may be made of protein, and may be pretreated with a repair material such as a hydrogel or collagen. U.S. Patent Application No. 20080031923 by Murray, et al. describes preparation of a collagen gel and a collagen-MATRIGEL™ gel which is applied to a torn ligament for repair of the ligament. These collagen matrices are mostly monocomponent devices.

A number of multicomponent ligament prosthesis have been described (see, e.g. U.S. Pat. Nos. 3,797,047; 4,187,558; 4,483,023, 4,610,688 and 4,792,336). U.S. Pat. No. 4,792,336 to Hlavacek, et al. discloses a device with an absorbable component comprising a glycolic or lactic acid ester linkage, and the remainder of the device comprising a non-absorbable component. The device includes a plurality of fibers comprising the absorbable component which can be used as a flat braid in the repair of a ligament or tendon. The required tensile strength is obtained by increasing the final braid denier. U.S. Pat. No. 5,061,283 to Silvestrini discloses a bicomponent device comprising polyethylene terepthalate and a polyester/polyether block copolymer for use in ligament repair. U.S. Pat. No. 5,263,984 to Li, et al, describes prosthetic ligament which is a composite of two densities of bioresorbable filaments. There is still a need for a device for repair of articular tissue such as the ligaments and tendons, with improved strength retention, load bearing capacity and ingrowth of new tissue.

It is an object of the present invention to provide a biocompatible device for repair, regeneration or reconstruction in articular injury which provides both mechanical and structure repair as well as forms a scaffold for ingrowth of cells to foam new tissue.

It is still another object of the present invention to provide a method for producing a device for repair, regeneration or reconstruction of articular injury which results in improved strength retention and ingrowth of new tissue.

It is also an object of the present invention to provide a method for repair, regeneration or reconstruction in articular injury which comprises implanting at the damaged area, a biocompatible polymeric device which supports ingrowth of cells and formation of new tissue, while simultaneously providing mechanical and structural support.

SUMMARY OF THE INVENTION

A device comprising at least three phases for repair or reconstruction of articular tissue injury such as torn ligaments and tendons has been developed. The device includes polymeric fiber-based degradable material and biocompatible non-degradable polymeric fiber-based material, in a three-dimensional braided scaffold. In a preferred embodiment the device is composed of three regions; two end sections designed for attachment of the device at the site of implantation, which allow for bone cell ingrowth, and a middle region which serves as a scaffold for ligament or tendon cell ingrowth, resulting in the replacement of a ligament or tendon. In this embodiment, the middle region differs from the two end-regions in size, braiding angle, porosity and/or polymer composition. The degradable material is designed to degrade after a period of about nine to twelve months, to allow for repair or augmentation of the ligament prior to the device losing the structural and mechanical support provided by the degradable material. The device is made using a process of braiding degradable and non-degradable polymeric fibers using a three-dimensional rotary braiding method or row and column method. In the preferred embodiment, the degradable material is poly(L-lactic acid) (PLLA) fiber and the non-degradable material is a polyester fiber.

Damaged articular tissue is repaired, regenerated, reconstructed, and/or augmented by implanting the device at a site of injury either during open surgery or arthroscopically. The two ends are secured into drilled bone tunnels using interference screws, rivets, or other attachment devices such as sutures. Torn or damaged ligament or tendon, or allograft tissue, may be sutured to or placed adjacent to the device to enhance healing or augmentation. The scaffold can also be modified for repair of other connective or articular injury, or other tissues.

DETAILED DESCRIPTION OF THE INVENTION

In the preferred embodiment, the device is used in the repair, regeneration, reconstruction or augmentation of articular injuries. Articular injuries include both intra-articular and extra-articular injuries. Intra-articular injuries involve, for instance, injuries to meniscus, ligament and cartilage. Extra-articular injuries include, but are not limited to, injuries to the ligament, tendon or muscle. These include injuries to the Anterior cruciate ligament (ACL), Lateral collateral ligament (LCL), Posterior cruciate ligament (PCL), Medial collateral ligament (MCL), Volar radiocarpal ligament, Dorsal radiocarpal ligament, Ulnar collateral ligament, Radial collateral ligament, meniscus, labrum, for example glenoid labrum and acetabular labrum, cartilage, and other tissues. The injury being treated may be, for instance, a torn or ruptured ligament. A ligament is a short band of tough fibrous connective tissue composed of collagen fibers. Ligaments connect bones to other bones to form a joint. A torn ligament is one where the ligament remains connected but has been damaged causing a tear in the ligament. The tear may be of any length or shape. A ruptured ligament is one where the ligament has been completely severed providing two separate ends of the ligament. A ruptured ligament may provide two ligament ends of similar or different lengths. The rupture may be such that a ligament stump is formed at one end. The repair of the damaged tissue is achieved using the partially degradable polymeric device in combination with mechanical devices, such as interference screws, sutures and anchors

I. Ligament or Tendon Repair Device

Figure 1:
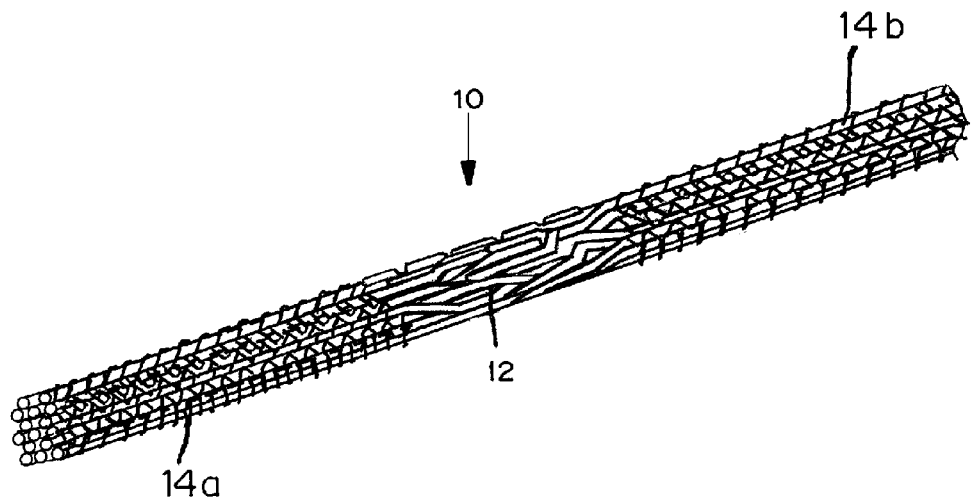
FIG. 1 is a perspective view of the multi-region ligament repair device.
Figure 2A:
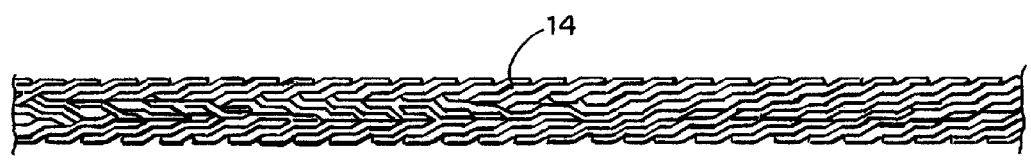
FIG. 2A is a perspective view of the bone attachment end of the device in FIG. 1.
Figure 2B:
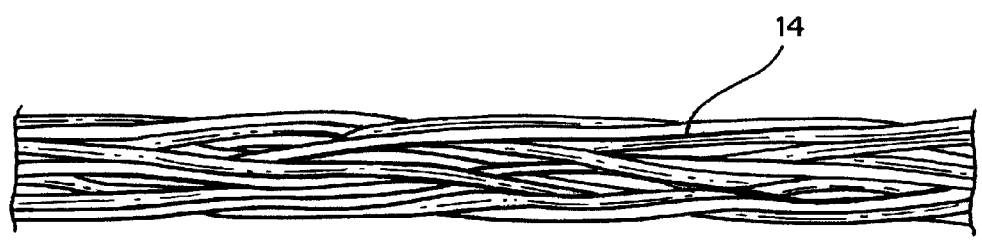
FIG. 2B is a perspective view of the ligament tissue scaffold center region of the device.

A multi-component polymeric device serves as a template for tissue regeneration as well as provides initial structural and mechanical support. The preferred ligament or tendon repair device 10 is shown in FIG. 1, based on hierarchical design methodology. The device is made up of degradable polymeric fiber and one or more non-degradable or very slowly degradable polymeric fiber materials. In a preferred embodiment the device is composed of three regions, with two end sections 14a, 14b designated for attachment of the device to the bone (shown in FIGS. 4A, 4B), and a middle region 12 which serves as the replacement articular tissue. In this embodiment, the middle region 12 differs from the two end regions 14a, 14b in size, braiding angle, porosity, and/or polymer composition (FIGS. 2A, 2B). The initial mechanical strength of the middle and end regions is preferably the same except for small differences caused by the extra braiding revolutions in the bony attachment region which slightly reduces strength. Ligament cell ingrowth occurs in the middle region and bone cell ingrowth occurs in the two end regions. Over time, the device begins to degrade. The end regions preferably degrade slower than the middle region due to the higher porosity of the middle region. The middle region may degrade at one rate, or have areas of different rates of degradation.

A. Polymeric Materials

As used herein, the degradable area is that which is replaced by cells and extracellular matrix as the polymer degrades. As used herein, the non-degradable component retains structural and mechanical properties as the degradable component degrades. The degradable region preferably degrades over a period of 9 to 12 months. The non-degradable region does not degrade prior to one to two years following implantation.

In some embodiments, the non-degradable material is made of a biocompatible non-degradable polymer. In other embodiments, the non-degradable component is a slowly degradable polymer. In still other embodiments, the non-degradable material used is a mixture of one or more non-degradable polymers and slowly degradable polymers. In these embodiments, the slowly degradable polymer is selected such that its rate of degradation is slower than the degradation rate for the polymer selected as the degradable component. In a preferred embodiment, degradation of the slowly degradable polymer occurs at 1-2 years. Complete degradation may not occur.

Suitable non-degradable polymers include polyethylene, polystyrene, silicone, polyfluoroethylene, polyacrylic acid, a polyaniide (e.g., nylon), polycarbonate, polysulfone, polyurethane, polybutadiene, polybutylene, polyethersulfone, polyetherimide, polyphenylene oxide, polymethylpentene, polyvinylchloride, polyvinylidene chloride, polyphthalamide, polyphenylene sulfide, polyetheretherketone ("PEEK"), polyimide, polymethylmethacylate and/or polypropylene. In some cases, the polymer may include a ceramic such as tricalcium phosphate, hydroxyapatite, fluorapatite, aluminum oxide, or zirconium oxide.

Suitable degradable polymers include polyhydroxy acids such as polylactic and polyglycolic acids and copolymers thereof, polyanhydrides, polyorthoesters, polyphosphazenes, polycaprolactones, biodegradable polyurethanes, polyanhydride-co-imides, polypropylene fumarates, polydiaxonane polycaprolactone, and polyhydroxyalkanoates such as poly4-hydroxy butyrate, and/or combinations of these. Natural biodegradable polymers such as proteins and polysaccharides, for example, extracellular matrix components, collagen, fibrin, polysaccharide, a cellulose, silk, or chitosan, may also be used.

Preferred biodegradable polymers are lactic acid polymers such as poly(L-lactic acid (PLLA), poly(DL-lactic acid (PLA), and poly(DL-lactic-co-glycolic acid) (PLGA). The co-monomer (lactide-glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50 can also be used. The preferred polymer for the non-degradable region is a polyester and the preferred polymer for the degradable region is poly(L-lactic acid (PLLA).

The proportion of the degradable to non-degradable component is selected such that the non-degradable component provides retained strength following degradation of the degradable component. In a preferred embodiment, the non-degradable component is less than 30% of the device. In a more preferred embodiment, the non-degradable component forms 10-30% of the device.

B. Cell Seeding

The devices can optionally be seeded with cells, preferably mammalian cells, more preferably human cells. Alternatively, they are implanted and cells may attach to and proliferate on and within the devices. Various cell types can be used for seeding. In a preferred embodiment, for ligament and tendon replacement, the cells are either mesenchymal in origin or capable of generating mesenchymal cells. Accordingly, preferred cell types are those of the connective tissue, as well as multipotent or pluripotent adult or embryonic stem cells, preferably pluripotent stem cells. For repair, regeneration or reconstruction of the ACL ligament, it may be preferable to seed the scaffold with ACL host cells, leaving stubs of the native ACL and implanting the device next to or into the stubs. However, the scaffolds can be seeded with any cell type which exhibits attachment and ingrowth and is suitable for the intended purpose of the braided scaffold. Some exemplary cell types which can be seeded into these scaffolds when used for repair, regeneration or augmentation of connective tissue or other tissue types such as parenchymal tissues, include, but are not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells.

Cells used are first harvested, grown and passaged in tissue cultures. The cultured cells are then seeded onto the three dimensional braided scaffold to produce a graft material composed of living cells and partially degradable matrix. Each region of the scaffold can be seeded. Osteoblasts or mesenchymal stem cells in the end region help regenerate bone, ligament. Mesenchymal stem cells in the middle region regenerate the ligament. This graft material can then be surgically implanted into a patient at the site of ligament or tendon injury to promote healing and repair of the damaged ligament or tendon.

Growth factors and other bioactive agents may be added to the graft material. In a preferred embodiment, these include fibroblast growth factor (FGF), vascular endothelial growth factor (VEGF), epidermal growth factor (EGF), and bone morphogenic proteins (BMPs). Adhesive materials such as fibronectin and vimentin can also be added. These are preferably added in amount ranging from 0.1 nanogram to 1 micrograms. Cell isolates (for example, from marrow cells) or biological factors isolated from blood can also be added to the graft or placed with the graft.

II. Methods of Manufacture

The device is prepared using standard equipment and techniques, modified to create multiple regions (two ends for attachment and at least one, two, three or more regions). The device is braided such that the middle region has adequate interfibrillar space and minimized thickness to promote the in-growth of tissue.

In the preferred embodiment, PLLA and polyester fibers are braided to form the three-dimensional braided devices. The device is braided, woven or knitted so that the structure has the desired strength and stiffness throughout the length of the device. In a preferred embodiment, a three-dimensional rotary braiding method or row and column method is used. Three-dimensional rotary braiding is similar to traditional two-dimensional-braiding technique except that it allows for greater flexibility of fiber placement in the braided structure by allowing for the movement of fiber bobbins independently and selectively in a flat array of horngears. This enables the production of fiber structures specifically designed for an intended end use. However, as will be understood by those of skill in the art upon reading this disclosure, other techniques for preparing three-dimensional braided scaffolds, including row and column methods, as disclosed can also be used.

Figure 3:
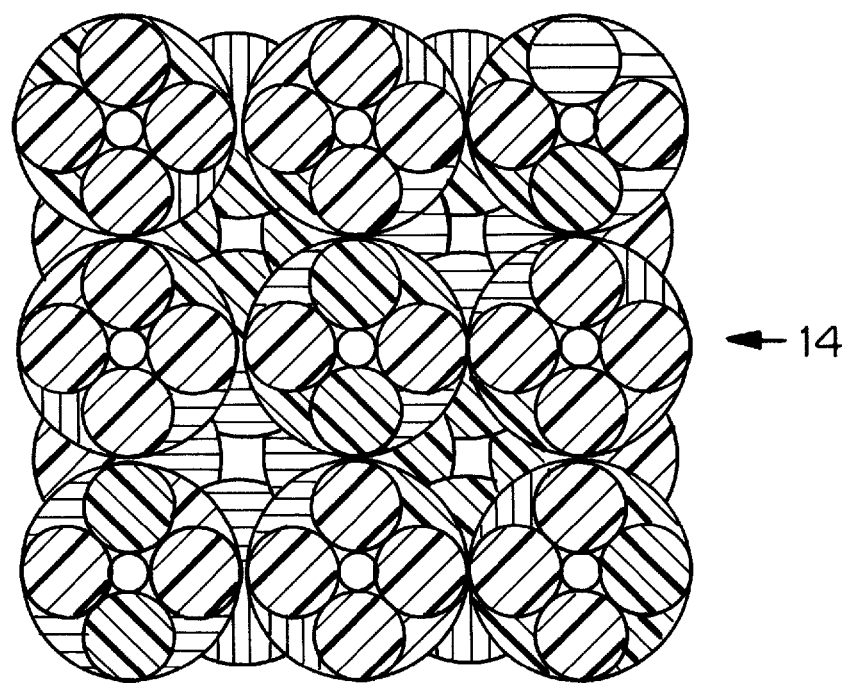
FIG. 3 is a perspective view of the end of the bone attachment end of the device shown in FIG. 2A.

The geometric parameters which determine the shape and fiber architecture of three-dimensional braids includes braiding angle distribution, yarn volume fraction, number of carriers, and braiding yarn width. The braiding pattern in turn depends on braiding machinery/technique used. A front view of the attachment end is shown in FIG. 3. The side view is shown in FIG. 2A. This contrasts with the looser braid of the middle region shown in FIG. 2B.

The device peak load strength range is from 500 to 3200 N, with an initial stiffness range of 200 to 700 N/mm. The number of fibers per bundle is in the range of 10 to 60 and the number of bundles per braid is in the range of 36, but it could be as low as 16 to as great as 64.

The key to the technology is the inclusion of at least three different regions, each with the specific pore size of the matrix to promote specific cell ingrowth. The typical range of porosity is between 50 and 70%, and pore size between 177 μm and 250 μm. In the two ends for attachment to bone, the pore size is designed to allow bone cell in-growth and the middle region is specifically designed to allow ligament cell in-growth.

The device is in contrast with prior art devices such as that in U.S. Pat. No. 4,792,336 which do not have regions for attachment at each end to provide both strength and bone in-growth, and a region in the middle which allows for ligament or tendon cell growth and retention of structural function until this can be replaced by the new tissue.

The devices are typically provided in a sterile kit, such as a foil or TYVEX® package. In a preferred embodiment, the device will include sutures or whip stitching in the graft, to facilitate placement. The kit will typically include screws, sutures, or other means for attachment.

III. Methods of Use

The device is used for repair, regeneration or reconstruction of articular injury, by implanting the multi-region polymeric device at a site in need of articular repair or reconstruction.

Implantation is performed using standard arthroscopic technique with two or three portals. A guide is drilled through the tibia with overdrill using a reamer on the tibia to tibial footprint area of the ACL, followed by insertion of the guide pin to the isometric point position over the femur near insertion of femoral insertion of the ACL. This is followed by an overdrill using a standard reamer on the femoral side. A Beath pin is then often used to complete drilling and the graft is then passed through the tibia and the femur. The graft is then secured using interference screws, or through the ENDOBUTTON® type technique. Visualization can be assisted using an arthrotomy. Preferably the graft is placed without an arthrotomy for a completely arthroscopically based technique.

Figures 4A, 4B:
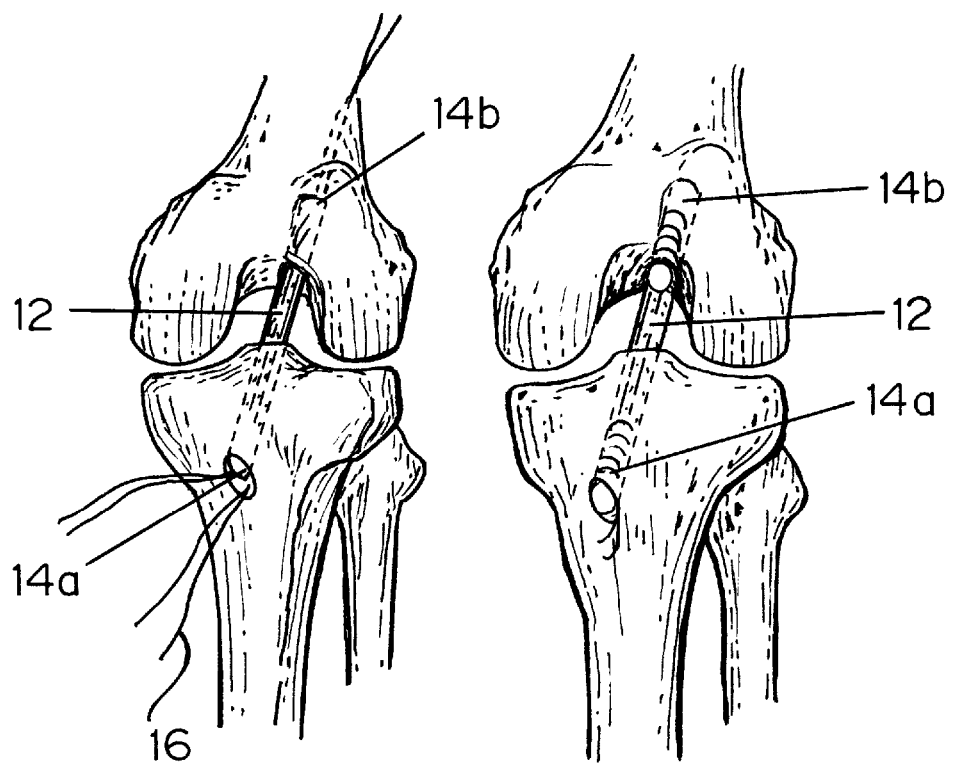
FIGS. 4A and 4B are prospective views of the implantation of the device to replace a torn ACL.

The ends 14a, 14b are placed in bone tunnels and secured with interference screws, rivets, sutures 16 or other techniques, as shown in FIGS. 4A and 4B. The device is intended to be implanted using the same techniques currently used by surgeons to implant patella tendon grafts.

In use, an appropriate number of the devices are implanted to match the biomechanical properties of the tissue being repaired. This permits an early return to normal function post-operatively. The implanted device bears applied loads and tissue in-growth commences. The mechanical properties of the biodegradable material of the implant slowly decay following implantation, to permit a gradual transfer of load to the ingrown fibrous tissue. In a preferred embodiment, the degradation of the biodegradable material occurs after about 9-12 months. Additional in-growth continues into the space provided by the biodegradable material of the implant as it is absorbed. This process continues until the biodegradable material is completely absorbed and only the newly formed tissue remains. The biocompatible non-absorbable material which is left following degradation of the degradable material provides long-term support for the newly formed tissue.

The following non-limiting examples are provided to further illustrate the present invention.

EXAMPLES

Example 1

Preparation of L-C Ligament Braid for Sheep Study

Materials and Methods
A one-meter length of L-C Ligament braid was prepared using a manual braiding machine to create a single fiber bundle until a total of 36 fiber bundles (each containing 24 fibers) have been created. Tie off the fiber bundle to the tie-off point located at the bottom of the braiding machine. Reduce the tension in the 36 fiber bundles. Fabricate 5-cm long section of "tight" braid. Tie-off end of the 5 cm long section of "tight" braid using a small piece of PLLA fiber that is two fibers measuring about 18 inches, doubled over to be 4 fibers 9 inches long. Fabricate 3-cm long section of "open" braid with one complete braiding revolution over the 3-cm long section. Tie-off end of the 3 cm long section of "open" braid using a small piece of PLLA fiber that is two fibers measuring about 18 inches, doubled over to be 4 fibers 9 inches long. Tighten. Cut off excess fiber leaving strands 1 inch long. Repeat until the braiding of the fiber bundles is complete at the top of the braiding machine. This yields 1 meter of braid containing 13 to 14 individual 8 cm Tiger Ligaments.

Example 2

Large Animal Study

A pilot large animal study involving 16 sheep was conducted at the University of New South Wales near Sydney Australia. The study was designed to evaluate, in a large animal model, the in vivo response of the L-C Ligament for use in tendon-bone reconstruction of an anterior cruciate ligament. The study evaluated the in vivo performance in terms of gross reaction in the knee joint, immunological reaction, radiographic evaluation in the bony tunnels, analysis of synovial fluid for polymeric debris, mechanical performance of the synthetic ligament, histological and pathological evaluation of the synthetic ligament in the bony tunnels and in the intra-articular space of the knee compared to a standard doubled over autograft tendon control at 12 weeks following implantation.

Materials and Methods
Animals:
Sixteen sheep were divided into four groups: four autografts (controls), four L-C ligaments, four tigers, and four autografts augmented with a L-C ligament.
Implants:
The autograft group consists of a doubled over extensor tendon.
L-C ligament is 100% PLLA, braided, measuring 8 cm in length, 2.5×2.5 cm, 4 mm cross-section.
Tiger is 83% PLLA and 17% polyester, braided, measuring 8 cm in length, 2.5×3×2.5 cm, 4 mm cross-section.
Method of Implantation:
ACL reconstruction was performed in the right hind limb of the sheep. 7 mm tunnels were drilled in the femurs and tibias. Titanium RCI screws (7×25 mm with an 8 mm head, Smith & Nephew) were used for fixation of the femoral and tibial tunnels.

Animals were inducted with an IM injection of Zoletil® for sedation. Anesthesia was achieved using Isoflurane and oxygen inhalation. All animals received 1 g of Cephalothin intravenously and 5 mls of Benacillin intramuscularly after induction as antibiotic prophylaxis. They also received buprenorphine (Temgesic, 0.006 mg/Kg, SC) and 4 mls of Carprofin (Rimadyl, SC) for pain relief prior to commencement of the surgical procedure. Twenty milliliters of blood were taken for routine pre-operative blood work.

Autograft Harvest
A 0.5 cm incision was made on the dorso-lateral aspect over the distal part of the metacarpals. Once the lateral extensor was completely free of the other extensors a modified Krachow stitch was inserted into the distal free end with #2 suture. The tendon was divided proximally using a tendon stripper, which cuts the tendon at the wrist where it exits a fibro-osseous tunnel laterally. The tendon grafts were removed and wrapped in saline soaked gauze. The harvest incision sites were closed with a resorbable 3-0 suture (Davis & Geck, North Ryde, Australia). The grafts will be kept moist with saline at all times during preparation. A Krackow stitch was placed at the other end of the grafts using #2 suture (Ethibond, Johnson and Johnson, North Ryde, NSW Australia).

Reconstruction

An infero-medial para-patellar incision was made. Dissection was continued down to the joint capsule, which was divided longitudinally. The skin edges and joint capsule were detracted to reveal the intra-articular fat pad typical of the ovine knee. The fat pad was partially excised to reveal the cruciate ligaments. The ACL was excised by division at its insertion into the tibia and femur, taking care not to damage the PCL. Cutting diathermy was used to excise the fat pad, but the ACL was excised with a knife to minimize intra-articular thermal injury. The attachment sites of the ACL to the tibia and femurweare noted and marked at this point.

The bone tunnels were made with a 4.5 mm cannulated drill bit over a guide followed by a 7 mm canulated drill. The tibial side was drilled from the medial border of the tibia, just distal to the tibial tuberosity. The guide was drilled first, exiting in the joint at the center of the tibial insertion of the ACL. The femoral side was drilled from the intra-articular surface outward. The tunnel was made from the posterior part of the femoral ACL insertion with the drill guide and cannulated drill as above. The tunnel exits proximally on the lateral surface of the lateral femoral condyle. The joint was thoroughly irrigated with saline. The graft was placed through the tibial tunnel into the knee joint and then into the femoral tunnel. Tension (~40N) was applied to the grafts during placement of the screws adjacent to the bone. The surgical sites were closed in layers with 3-0 Vicryl (Johnson and Johnson, North Ryde, Australia) and the skin closed with 3-0 Dexon (Davis & Geck, North Ryde, Australia). The sites were cleaned and sprayed with Op-site spray.

Post-Operative Monitoring and Recovery

Sheep were free to mobilize in their pen and fully weight bear. No splints were used at any time. The sheep were monitored daily in the first week and weekly thereafter for signs of swelling, infection, bleeding, haematoma or general ill health.

Assessments of Clinical Function

Clinical assessment of laxity and lameness at the time of surgery were qualitatively assessed based on a lameness score. A score of 0 represents a lame animal that cannot load bare; 1 slight load bearing; 2 partial load bearing and 3 full load bearing. Clinical assessments were made on weeks 1, 4, and 8 weeks as well as before euthanasia at 12, 26 and 52 weeks.

A functional test of anterior draw was performed at the time of sacrifice to assess overall laxity in the same manner as the post operative evaluation.

Animals were killed via lethal injection using Lethobarb at the designated time point. The right hindlimbs were harvested for experimental endpoints. The left distal femur was harvested for testing of the contralateral limb. Twenty mls of blood was taken for routine blood work at euthanasia. This blood work was used to confirm overall animal health status.

A post-mortem analysis was performed on the internal organs (heart, liver, kidney) as well as lymph nodes. These tissues were photographed and a portion sharply dissected and placed into phosphate buffered formalin for routine histology. Paraffin sections were stained with H&E and examined under normal and polarized light for histological appearance and the presence of any polymeric wear debris.

An anterior draw test was performed after sacrifice to examine overall knee stability with the knee in 30 degrees of flexion. The knees were graded as lax or stable.

Mechanical Testing

Mechanical testing was performed at 12, 26 and 52 weeks as well as at time zero on cadaver knees with new devices using the reported technique of (Rogers et al., 1990; Walsh et at, 2007). Mechanical testing was performed on the femur-graft-tibia complex. The right and left hind limbs were tested using a calibrated servo-hydraulic testing machine (MTS 858 Bionix, MTS Corporation, MN). The femur and tibia with the knee capsule intact were placed into a drill template jig for preparation for mounting. This is done to avoid any rotation of the femur or tibia during drilling and provide a reproducible test set-up. Two drill holes are placed in the diaphysis of the femur and tibia based on the mounting template to ensure reproducible placement of the samples. The mounting template oriented the samples at 45 degrees of flexion to enable the load and displacement properties to be measured in an anterior draw loading profile.

The knees were dissected following drilling of the mounting holes. The capsule was carefully reflected using an anteromedial incision and placed in formalin for histological analysis described in the histology section. The medial and lateral menisci were removed with meticulous dissection taking care not to damage the intra-articular graft. The menisci were placed in formalin for subsequent histology. The status of the articular cartilage on the femur and tibia were noted and photographed. The dissection was completed after the mounting holes were drilled. This enabled reproducible orientation of the femur and tibia without any rotation or translation.

The samples were tested in anterior draw orientation (45 degrees) using a preconditioning profile of 10 cycles followed by a stress relaxation period prior to testing to failure at 50 mm/minute. The peak load, energy to pull out and linear stiffness and failure mode and site were determined for all samples. Mechanical data was analyzed using analysis of variance followed by a Games Howell Post Hoc test with SPSS for Windows.

Synovial Fluid Analysis

Synovial fluid in the synthetic ligament group was analyzed for evidence of polymeric debris at the time of harvest. The fluid present was collected with an 18 gauge needle and a 20 ml syringe. The fluid within the syringe was photographed and the color noted. A sample of the fluid was placed on a microscope slide and examined under polarized light for the presence of any polymeric debris.

Computed Tomography

Computed tomography (CT) was performed on the right femur and tibia (tendon-bone reconstruction side). CT scans were performed perpendicular to the long axis of the femur and tibia using a Toshiba Scanner (Tokyo, Japan). Slice thickness was set to 0.5 mm for all scans. CT scans was stored in DICOM format. The DICOM images was viewed using MIMICS (Materialise, Belgium). Three dimensional models was reconstructed based and examined in the axial, sagittal and coronal planes.

Micro Computed Tomography

Micro Computed tomography (CT) was performed on the right femur and tibia (tendon-bone reconstruction side). CT scans was performed perpendicular to the long axis of the femur and tibia using a Inveon Scanner (Siemens, USA). Slice thickness was set to 50 microns for all scans. CT scans was stored in DICOM format. The DICOM images was viewed using MIMICS (Materialise, Belgium). Three dimensional models was reconstructed based and examined in the axial, sagittal and coronal planes.

JPEG images of the DICOM images was provided in the report. Screw, tendon-bone and screw-bone interactions was qualitatively addressed in a more detailed fashion through the use of micro CT.

Magnetic Resonance Imaging

MRI was performed on the animals dedicated for histology. The right and left hind-limbs was scanned using a 3T MRI intact prior to dissection. MR images was analyzed for signal intensity of the intra-articular portion of the graft to assess for overall status of healing compared to the contralateral side using T2 weighted images.

Histology Right Tibia and Femur

The right tibias were processed for histology by fixation in cold phosphate buffered formalin for a minimum of 72 hours with 2 changes of formalin. Following adequate fixation, the tibias were roughly cut back with a hack saw to isolate the tibial tunnels and the surrounding bone. The isolated bone tunnels will be dehydrated in ethanol and embedded in PMMA. Polymerized blocks were cut perpendicular to the long axis of the bone tunnel in 5 mm blocks using a Buelher saw. The blocks were Faxitroned, polished and examined for bone ingrowth and integration with the synthetic ligament using an environmental electron microscope (Hitachi TM1000). The screw-graft and graft-bone interface were examined for evidence of ingrowth and interaction as well as adverse events such as bone resorption.

A final section from each block were cut for routine light histology using a Leica SP 1600 Microtome. The histological interface between the graft, screw and tunnel will be evaluated in terms of bony response or adverse reactions in any.

The intra-articular portion of the right and left knees were harvested and the femoral insertion marked with 7-0 suture. These samples were processed in PMMA following alcohol dehydration. The blocks were sectioned using a Leica microtome. Sections were stained with H&E and Tetrachrome to evaluate the new tissue infiltration. The cellular population and degree of infiltration were compared versus time. The histology was compared to the intact left non-operated sides at each time point.

The medial and lateral capsular tissues from the right and left knees were processed for routine paraffin histology and H&E staining. These sections were compared to determine if the presence of the graft or the surgical procedure resulted in a change in the synovium.

A sample of the articular cartilage from the medial femoral condyle and medial tibial will be harvested. The cartilage samples will be fixed in formalin and decalcified in formic acid. Sagittal sections will be embedded in paraffin and sections stained with H&E and Saf O to examine any changes in the articular cartilage due to surgery or the presence of the synthetic graft.

A sample of the medial menisci from the right and left knees were harvested. The samples were fixed in formalin and processed for paraffin histology. The sections were stained with H&E to examine any changes in the menisci due to surgery or the presence of the synthetic graft.

Results

A key objective of the study was to examine the initial response of a traditional ACL autograft repair compared to an ACL reconstruction using the L-C Ligament™, a 100% biodegradable synthetic graft. Using an adult sheep model, the study examines numerous in vivo performance factors at various time horizons. The endpoints evaluated in the study include post-operative recovery, clinical assessment of animal laxity and lameness, gross reaction in the knee joint, immunological reaction, radiographic evaluation in the bony tunnels, analysis of synovial fluid, as well as histological and pathological evaluation of the L-C Ligament™, in the bony tunnels and in the intra-articular space of the knee compared to a standard doubled over (four stranded) autograft tendon control at various time points following implantation.

Following initial implantations, the test animals were clinically assessed and monitored for lameness and load bearing ability on a fixed schedule. All subjects treated with synthetic grafts showed superior recoveries as compared to those treated with autografts. This is, in part, due to the lack of harvest site morbidity as seen in the autograft model. Study animals experienced partial load bearing during the first 1 to 3 days and had increased load bearing thereafter. When the initial sacrifices occurred, all animals had a normal gait based on a qualitative lameness score.

Approximately 12 weeks after implantation, several study animals were sacrificed for a macroscopic examination as well as histological, radiographic and pathological evaluation. A post-mortem analysis was performed on the key internal organs as well as the lymph nodes. There was no indication of any adverse events.

Radiographic imaging analysis of the reconstructed limbs, which included x-rays and magnetic resonance imaging (MRI), confirmed the placement of the fixation screws after 12 weeks. A coronal view of the micro computed tomography (micro CT) at 12 weeks displayed two titanium interference screws and the L-C Ligament™ synthetic graft. The screws were well placed in the femora and tibial tunnels, and a new interface along the margins of the tunnels were noted on the CT scans, suggesting a healing bone-tunnel interface was in progress at 12 weeks following surgery. The micro CT images also demonstrated that there was no widening of the femoral or tibial bone tunnels. This was a positive and important finding.

Macro dissection of the L-C Ligament™ study animals showed no sign of adverse reaction in the knee joint and the synovial fluid was clean and free of debris. Furthermore, at 12 weeks, animals implanted with the synthetic ligaments had fibrous tissue completely encompassing the graft at the intra-articular zone. Cross-sections of the synthetic grafts also revealed visible tissue inside the L-C Ligament™, both in the intra-articular area and on the tibial surface. These macro findings are all significant signs of healing and are indicative of a strong regenerative response.

A detailed histology of the animals sacrificed at 12 weeks confirmed the macroscopic findings. The intra-articular portion of the L-C Ligament™ graft, and distal and proximal tibia were harvested, dehydrated and embedded in poly methylmethacrylate (PMMA), stained with methylene blue/fuschin, and analyzed by light microscope. Sections were cut perpendicular to the long axis of the screw through the femoral tunnel. The intra-articular portion was sectioned perpendicular to the long axis of the graft, and the tibial tunnels were sectioned in the proximal as well as mid portion of the tunnel perpendicular to the long axis of the screw.

The histological study of the L-C Ligament™ animals all showed strong evidence of ligamentization in the intra intra-articular area as well as fibrous tissue integration in the entrance of the tibial bone tunnel (the fixation point). The process of ligamentization was characterized by integration and remodeling new tissue into the intra-articular portion of the graft. Historically, tissue infiltration at the point of fixation has been the major shortfall of many similar research efforts.

The synthetic graft was easily seen in sections perpendicular to the long axis of the screw through the femoral tunnel, when viewed under polarized light at the 12 week time point. The graft appeared intact with no macroscopic evidence of degradation. The graft was well fixed in the femoral tunnel and thickening of the cancellous bone at the margins of the drill and graft was evident. New fibrous tissue was found integrating into the graft. Multinucleated cells were present along the soft tissue-bone interface. Under higher magnification, plump fibroblastic cells and new connective tissue were seen in the new soft tissue integrating into the device. No evidence of resorption on the PLLA was found at 12 weeks, and the PLLA fibers appeared intact.

The intra-articular portion, sectioned perpendicular to the long axis of the graft, revealed the presence of the PLLA fibers with new fibrous tissue integrating into the spaces present between the fibers. Higher magnification demonstrated similar fibrous tissue integration into the graft and the presence of fibroblastic cells as noted in the bone tunnels.

Sections of the proximal portion of the tibial tunnels were also analyzed at the 12 week time point. These sections were in the bone tunnel, however, the screw was not present in these sections, indicating the sections were above the screw. The synthetic graft was surrounded by bone when viewed under polarized light. The graft appeared intact with no macroscopic evidence of degradation and new fibrous tissue was seen infiltrating into the graft. Under higher magnifications, the PLLA fibers appeared intact and new fibrous tissue and collagenous tissue were found integrating into the PLLA fibers.

Sections in the graft-screw interface in the middle of the tibial tunnel were analyzed. In these sections, the whip stitching on the graft can be seen with the screw compressing the graft against the tunnel. A closer examination of the interface within the tibial tunnel where the screw is compressing the graft reveals integration at the margins and stable fixation of the graft. The interface is fibrous in nature with fibroblastic cells as newly formed connective tissues.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A device for replacement or regeneration of articular tissue comprising
    polymeric fibers degrading at between nine and twelve months following implantation, and
    polymeric fibers not degrading following implantation in less than one year,
    wherein bundles of the polymeric fibers are braided into a three-dimensional braided scaffold to form two end sections for attachment of the device at a site of implantation and at least one middle section between the end sections, wherein the polymer of the middle section degrades more rapidly or the middle section is more porous than the end sections,
    wherein the device has a peak load strength range from 500 to 3200 N, with an initial stiffness range of 200 to 700 N/mm,
    wherein the number of fibers per bundle is in the range of 10 to 60 and the number of bundles per braid is in the range of 16 to 64,
    wherein the polymeric braid of the middle section of the device has a porosity between 50 and 70%, and pores between 177 µm and 250 µm in diameter, and
    wherein the device provides articular tissue function at the site of implantation as tissue integrates into the device.

2. The device of claim 1 for ligament or tendon repair, wherein the end sections are attachable to bone and allow for ingrowth of bony tissue.

3. The device of claim 2 wherein the porosity of the middle section allows in-growth of connective tissue.

4. The device of claim 1 produced by a three-dimensional rotary braiding method or row and column method.

5. The device of claim 1, wherein the middle section differs from the end sections in size, braiding angle, or porosity.

6. The device of claim 1 wherein between 70 and 90% of the polymeric fibers are degradable in less than one year.

7. The device of claim 1 wherein the degradable polymer fibers are made up of polymers selected from the group consisting of poly(L-lactic acid (PLLA), poly(DL-lactic acid (PLA), poly(DL-lactic-co-glycolic acid) (PLGA), polyorthoesters, polyanhydrides, polyphosphazenes, polycaprolactones, polyhydroxyalkanoates, biodegradable polyurethanes, polyanhydride-co-imides, polypropylene fumarates, polydiaxonane, polysaccharides, collagen, silk, chitosan, and celluloses.

8. The device of claim 1 wherein the non-degradable polymer fibers are made up of polymers selected from the group consisting of polyethylene terephthalate (PET), polyetheretherketone (PEEK), polytetrafluoroethylene (PTFE), polyester, polyethylene, polyamide, polyimide, polyurethane, polybutadiene, polybutylene, and polypropylene.

9. The device of claim 1, wherein the device is seeded with cells, ingrowth of which is supported by the scaffold.

10. The device of claim 9 wherein the cells are selected from the group consisting of mesenchymal cells, cells generating mesenchymal cells, fibroblasts, pluripotent stem cells, and multipotent stem cells.

11. A method for repairing, regenerating, replacing or reconstructing a damaged tendon or ligament in a patient comprising implanting at a site of a damaged tendon or ligament the device of claim 1.

12. A kit comprising the device of claim 1 and means for attachment.

13. A method of making the device of claim 1 comprising braiding a three-dimensional scaffold comprising
    polymeric fibers degrading at between nine and twelve months following implantation, and
    polymeric fibers not degrading following implantation in less than one year,
    wherein the polymeric fibers are braided into a three-dimensional braided scaffold to form two end sections for attachment of the device at a site of implantation and at least one middle section between the end sections, wherein the polymer of the middle section degrades more rapidly or the middle section is more porous than the end sections,
    wherein the device provides articular tissue function at the site of implantation as tissue integrates into the device.

14. A device for replacement or regeneration of articular tissue comprising
    bundles of fibers formed of polymer degrading following implantation,
    wherein the bundles of the polymeric fibers are braided into a three-dimensional braided scaffold to form two end sections for attachment of the device at a site of implantation and at least one middle section between the end sections, wherein the middle section is more porous than the end sections, wherein the device has a peak load strength range from 500 to 3200 N, with an initial stiffness range of 200 to 700 N/mm, and wherein the device provides articular tissue function at the site of implantation as tissue integrates into the device.

15. The device of claim 14 wherein the fibers in the bundles are multifilament fibers.

* * * * *